United States Patent
Engvall et al.

(10) Patent No.: US 9,854,980 B2
(45) Date of Patent: Jan. 2, 2018

(54) DEVICE FOR MONITORING BLOOD LEAKAGE FROM WOUNDS

(71) Applicants: REDSENSE MEDICAL MALTA LTD, Msida (MT); Daniel Engvall, Halmstad (SE)

(72) Inventors: Daniel Engvall, Halmstad (SE); Anders Nilsson, Halmstad (SE)

(73) Assignee: REDSENSE MEDICAL MALTA LTD, Msida (MT)

( * ) Notice: Subject to any disclaimer, the term of this patent is extended or adjusted under 35 U.S.C. 154(b) by 492 days.

(21) Appl. No.: 14/389,695

(22) PCT Filed: Mar. 22, 2013

(86) PCT No.: PCT/SE2013/000041
§ 371 (c)(1),
(2) Date: Sep. 30, 2014

(87) PCT Pub. No.: WO2013/147670
PCT Pub. Date: Oct. 3, 2013

(65) Prior Publication Data
US 2015/0094598 A1    Apr. 2, 2015

(30) Foreign Application Priority Data
Mar. 30, 2012    (SE) ...................... 1230031

(51) Int. Cl.
*A61B 5/00*    (2006.01)
*A61B 5/02*    (2006.01)
(Continued)

(52) U.S. Cl.
CPC ........ *A61B 5/02042* (2013.01); *A61B 5/0059* (2013.01); *A61B 5/150961* (2013.01);
(Continued)

(58) Field of Classification Search
CPC ................................ A61B 2562/228
See application file for complete search history.

(56) References Cited

U.S. PATENT DOCUMENTS

| 7,641,612 B1 | 1/2010 | McCall |
| 2003/0128125 A1 | 7/2003 | Burbank et al. |

(Continued)

FOREIGN PATENT DOCUMENTS

| DE | 102009051993 A1 | 5/2011 |
| JP | 2011-092514 A | 5/2011 |
| WO | WO 2006/001759 A1 | 1/2006 |

OTHER PUBLICATIONS

"Kientec—ST-Medical Connector—stainless steel or ceramic ferrule with custom ID's", Sep. 24, 2010, https://web.archive.org/web/20100924165403/http://www.kientec.com/connectors_st.htm. Retrieved from the internet on Aug. 13, 2015, XP055207745.
(Continued)

*Primary Examiner* — Michael Kahelin
*Assistant Examiner* — Farshad Negarestan
(74) *Attorney, Agent, or Firm* — Birch, Stewart, Kolasch & Birch, LLP (57) ABSTRACT

A device for monitoring a skin surface for leakage of blood at, for example, a wound or a vascular access. The device comprises a patient unit, a connection unit and a monitor unit. The patient unit comprises a patch, including an adhesive layer to be attached to the skin surface of the patient. The adhesive layer is arranged to attach the patch to the skin so that a predetermined removal force, such as 30N, is required for removing the patch from the skin surface. A patient optical fiber is arranged at the patch and has a proximal end for connection to the connection unit. A patient connector is arranged at the distal end of a connection optical fiber. The connector has an opening passing through the connector, whereby the connection optical fiber is
(Continued)

arranged in one end of the opening. The patient optical fiber may be inserted in the other end of the opening so that the proximal end of the patient optical fiber is arranged in register with the distal end of the connection optical fiber in order to transmit light between the optical fibers. A spring is arranged in the connector for exerting a force at the patient optical fiber at a side surface thereof for preventing unintentional withdrawal of the patient optical fiber. However, when the withdrawal force is larger than the removal force of the patch, the patient optical fiber is withdrawn from the connector. Thus, the patch is not removed from the skin even when a large force is exerted on the optical fibers.

11 Claims, 9 Drawing Sheets (51) Int. Cl.
*A61M 1/36* (2006.01)
*A61B 5/15* (2006.01)
*A61B 5/157* (2006.01)

(52) U.S. Cl.
CPC .......... *A61B 5/6832* (2013.01); *A61B 5/6833* (2013.01); *A61M 1/3653* (2013.01); *A61M 1/3656* (2014.02); *A61B 5/15003* (2013.01); *A61B 5/157* (2013.01); *A61B 5/150969* (2013.01); *A61B 5/445* (2013.01); *A61B 2560/0406* (2013.01); *A61B 2560/0412* (2013.01); *A61B 2562/0233* (2013.01); *A61B 2562/223* (2013.01); *A61B 2562/228* (2013.01); *A61B 2562/242* (2013.01); *A61M 2205/15* (2013.01); *A61M 2205/3306* (2013.01)

(56) References Cited

U.S. PATENT DOCUMENTS

| | | |
|---|---|---|
| 2005/0038325 A1 | 2/2005 | Moll |
| 2006/0130591 A1 | 6/2006 | Perkins |
| 2007/0004996 A1 | 1/2007 | Lovejoy et al. |
| 2008/0195021 A1 | 8/2008 | Roger et al. |
| 2008/0195060 A1 | 8/2008 | Roger et al. |
| 2008/0249487 A1 | 10/2008 | Engvall |
| 2009/0082649 A1 | 3/2009 | Muller et al. |
| 2009/0088613 A1 | 4/2009 | Marttila et al. |

OTHER PUBLICATIONS

"The Fiber Optic Association—Tech Topics: Connector Identifier", Nov. 4, 2011, p. 5, lines 13-16, https://web.archive.org/web/20111104220323/http://www.thefoa.org/tech/connID.htm. Retrieved on Aug. 13, 2015, XP055207750.

Extended European Search report dated Aug. 25, 2015 for Application No. 13767355.4.

International Search Report dated Aug. 2, 2013 for International Application No. PCT/SE2013/000041.

International Search Report dated Oct. 29, 2012 for Application No. ITS/SE12/00135.

DEVICE FOR MONITORING BLOOD LEAKAGE FROM WOUNDS

FIELD OF INVENTION

The present invention relates to a device for monitoring of blood leakage from wounds. One particular field is monitoring of vascular access of a patient during extracorporeal treatment, such as dialysis.

BACKGROUND

WO2006/001759A1 issued to the assignee of the present invention, discloses a method and means for detection of blood leakage from wounds by means of an optical fiber. The optical fiber is arranged in a loop from a light source to a patch to be attached to the patient and back to a light detector. The light source and light detector are arranged in a monitoring device at a distance from the patch and may be attached to the arm of a patient. The loop comprises a sensor portion arranged at the patch and in which the optical fiber is bent with a small radius, so that the total internal reflection angle inside the optical fiber is approached or exceeded. A portion of the light transmitted through the optical fiber passes out through the sidewall of the optical fiber in the small radius sensor portion. When the sensor portion is exposed to a fluid, such as water or blood, the portion of the light passing out through the sidewall of the optical fiber in the small radius sensor portion increases, which may be sensed by the light detector as a decrease in light intensity, which may trigger an alarm.

The device according to WO2006/001759A1 operates well and is able to monitor for example a vascular access in an extracorporeal treatment, such as dialysis.

However, the manufacturing costs of said device may be further decreased. In addition, the amount of surplus material during manufacturing may be reduced. Furthermore, the security of the connection of the patient device to the monitor may be improved. However, a reduction of costs and operation requires a new technology to be used.

It is noted that the patient portion should be sterile and is disposable. However, the monitoring unit including the light source and detector and further electronic circuits is reusable. Thus, a reduction of costs per treatment may be obtained by reducing the costs of the disposable patient portion.

Another problem is relocation of the patch when the optical fiber is exposed to a force. When the patient is moving, the optical fiber may be influenced upon resulting in the fact that the patch is removed. This may remain unnoticed for a long time. When it is noticed, it is sometimes difficult to relocate the patch and it may be required to attach a new patch. If the relocation remains unnoticed, this is a safety risk.

SUMMARY OF THE INVENTION

Accordingly, an object of the present invention is to mitigate, alleviate or eliminate one or more of the above-identified deficiencies and disadvantages singly or in any combination.

In an aspect, there is provided a device for monitoring a skin surface for leakage of blood at a monitoring position, for example a wound or a vascular access. The device comprises a patient unit, a connection unit and a monitor unit. The patient unit comprises a patch, including an adhesive layer to be attached to the skin surface adjacent the monitoring position, whereby the adhesive is arranged to attach the patch to the skin so that an approximate predetermined removal force is required for removing the patch from the skin surface. The patient unit further comprises a patient optical fiber having an exposed distal end arranged in the patch and a proximal end for connection to the connection unit. The connection unit comprises a connection optical fiber, the distal end of which comprises a connector having an opening passing through the connector from one end to the other. The connection optical fiber is arranged in one end of the opening and the patient optical fiber may be inserted in the other end of the opening for being arranged with the proximal end of the patient optical fiber in contact with and in register with the distal end of the connection optical fiber. A spring is arranged in the connector for exerting a force at the patient optical fiber at a side surface thereof for preventing withdrawal of the patient optical fiber, until a predetermined withdrawal force is exerted on the patient optical fiber, whereby the withdrawal force is smaller than said removal force.

The proximal end of the patient optical fiber may be formed in that the optical fiber including its cover is cut at a substantially right angle or peeled and cut at a substantially right angle. The proximal end of the patient optical fiber may be polished, for example during the cutting operation.

The distal end of the patient optical fiber may be arranged for reflecting light passing along the optical fiber by total inner reflection when the distal end of the patient optical fiber is surrounded by air. Thus, the distal end of the patient optical fiber may be conical or frusto-conical or semi-spherical.

The connector comprises a cylindrical opening for receiving the proximal end of the patient optical fiber. The cylindrical opening has a diameter which is equal to or slightly larger than the outer diameter of the patient optical fiber, inclusive its cover.

The connector may comprise a radial spring member, which is arranged so that it normally covers an entrance to said cylindrical opening. The spring member may further comprise a hole, which may be moved into register with said cylindrical opening against a spring action by said spring member, whereby entrance of the patient optical fiber is enabled. When the spring is released, the hole exerts a force on the patient optical fiber. There may be arranged a second spring member inside the cylindrical opening, for example extending in the opposite direction compared to the first spring member.

For visual inspection of the connection point between the patient optical fiber and the connection optical fiber, there may be arranged a side hole between the connection point and the side surface of the connector.

BRIEF DESCRIPTION OF THE DRAWINGS

Further objects, features and advantages of the invention will become apparent from the following detailed description of embodiments of the invention with reference to the drawings, in which.

DETAILED DESCRIPTION OF EMBODIMENTS

Below, several embodiments of the invention will be described. These embodiments are described in illustrating purpose in order to enable a skilled person to carry out the invention and to disclose the best mode. However, such embodiments do not limit the scope of the invention. Moreover, certain combinations of features are shown and discussed. However, other combinations of the different features are possible within the scope of the invention.

The general operation of a device according to the invention is the following. A patch is attached to the patient adjacent the site to be monitored, such as a vascular access of a dialysis patient. The patch comprises a compress for absorbing blood emitted from the vascular access, which is an indication of an alarm condition.

Embedded inside the patch is a distal end of an optical fiber, which may be shaped as a cone and is exposed to the surrounding atmosphere, which is air, inside the compress. The proximal end of the optical fiber is connected to a light transmitter and a photo detector. Light transmitted through the optical fiber towards the distal end is normally reflected back 180 degrees to the photo detector by total internal reflection at the distal end surface of the fiber. If blood reaches and is contacting the exposed conical surface of the optical fiber, the total internal reflection disappears at the contacting area and light passes out through the distal end of the fiber. Then, the signal level at the photo detector decreases, which may cause an alarm or an alert situation. The expression proximal and distal are as seen from the monitor side, which means that the distal end is closest to the needle, catheter or wound to be monitored for bleeding.

Bleeding may occur if a venous needle of a vascular access is removed during treatment. Normally, during an extracorporeal treatment, such as dialysis, blood is returned to the body via a venous needle. In such a treatment, the blood flow may be about 200 to 500 ml/min. If the venous needle accidentally is removed from the vein, the returning blood flow passes out of the needle instead of being returned to the patient. If such a situation remains unnoticed for only 2 minutes, a life threatening condition develops. However, when the venous needle is dislocated, blood is emitted and may be detected adjacent the blood access location. Often, the venous needle is rapidly removed far away from the access site, for example down the floor. However, the venous needle will emit a sufficient amount of blood to be detected at the access site even at a rapid removal. However, sometimes the blood left at the access site is very small, only a droplet, and the bulk of the blood is discharged for example at the floor. In addition, blood may leak from the vein and out through the hole in the skin left by the venous needle, at least for a short time duration. During the extracorporeal treatment, blood is also removed from a patient via an arterial needle. If such an arterial needle is removed or dislocated, this is not particularly dangerous, since such a dislocation only results in that blood is not removed out to the extracorporeal circuit, which only results in that the desired treatment is not achieved. However, the arterial needle access can also be monitored by the present embodiments of the invention. Also, other sites on the skin of a patient may be monitored for blood, such as a wound.

Figure 1:
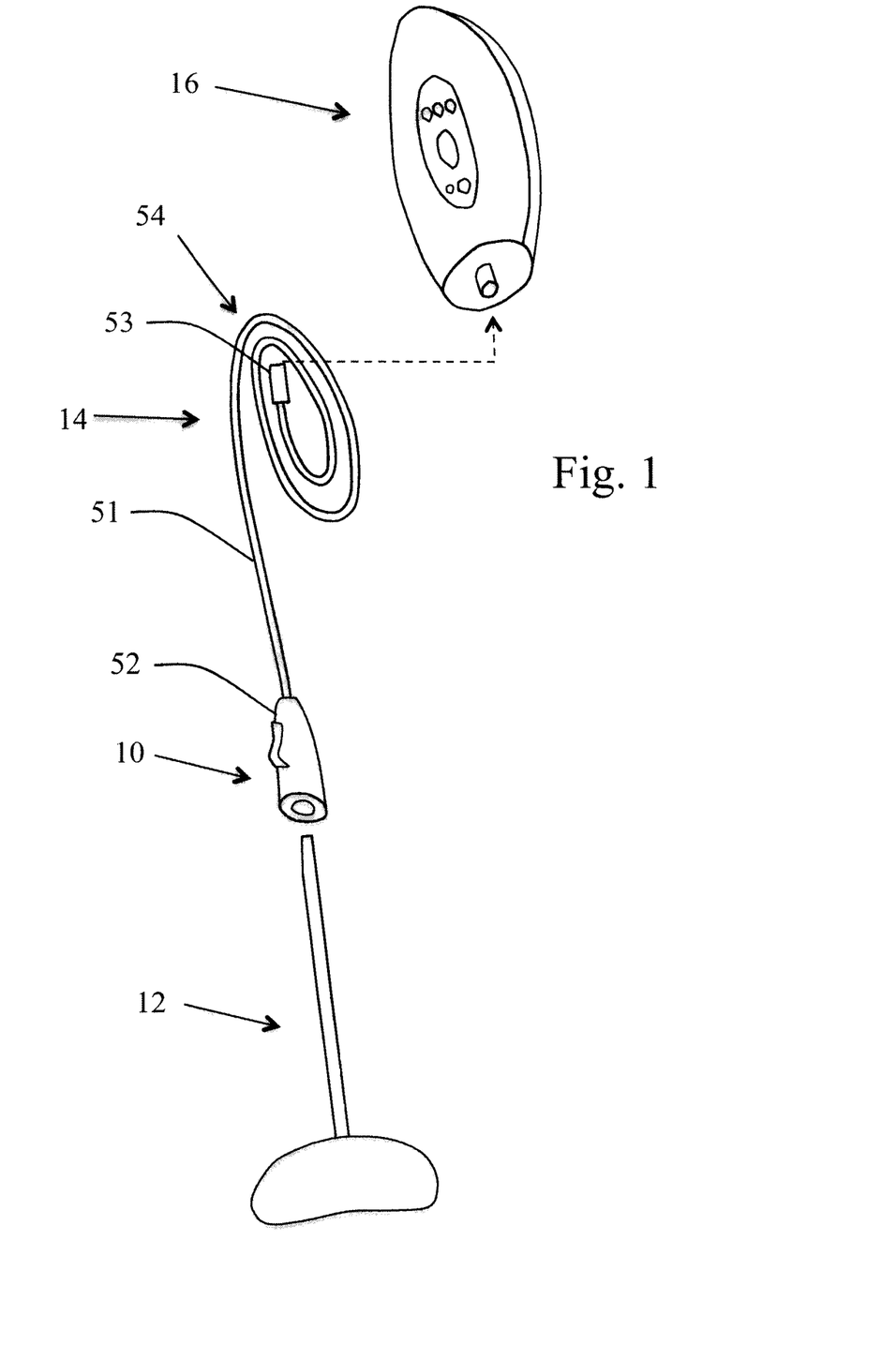
FIG. 1 is a schematic view of an embodiment of the monitoring device according to the invention.

FIG. 1 is a schematic overview of the components of a device 10 according to a first embodiment of the invention. The device 10 according to the first embodiment comprises a patient unit 12, a connection unit 14 and a monitor unit 16. The patient unit 12 is intended for attachment to a patient adjacent a wound or a vascular access to be monitored. The monitor unit 16 comprises electronic devices for monitoring the patient unit 12. The connection unit 14 is for connection of the patient unit 12 to the monitor unit 16.

Figure 2:
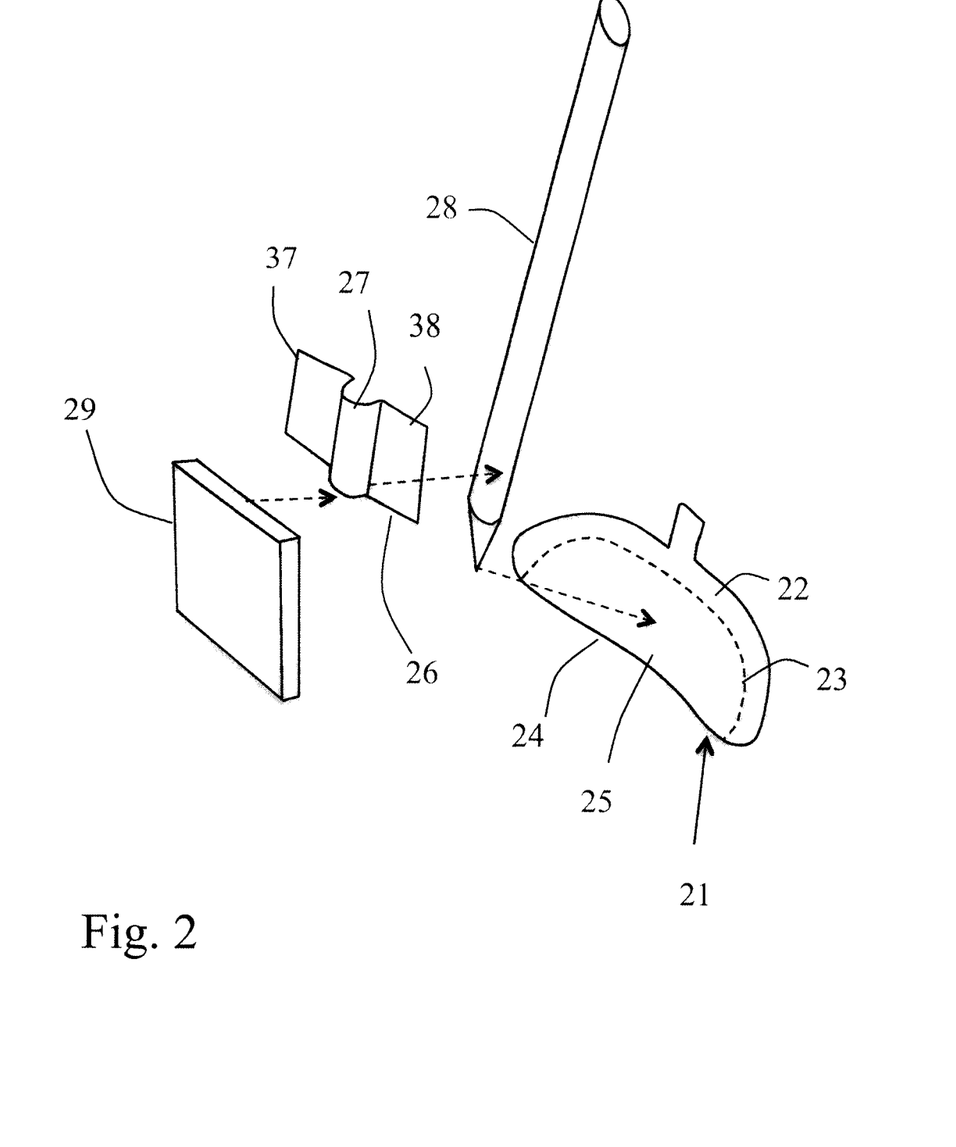
FIG. 2 is an exploded view of the patient unit.

The patient unit 12 is shown in more detail in FIG. 2. The patient unit comprises a patch 21 of a flexible web material. The patch is covered by a plastics material 22 at the bottom side as seen in FIG. 2, over at least a portion thereof, as shown by broken lines 23. The bottom side is facing away from the skin the patch is applied to the skin in a monitoring position. In addition, the upper side of the patch is partly covered by an adhesive layer 24 protected by a removable layer 25. By removing the removable layer 25, the adhesive layer 24 becomes exposed and may attach the patch to the skin of a patient, for example adjacent a vascular access. The adhesive is dimensioned so that a specific removal force is required for removing the patch from the skin surface. Such a removal force may be about 30 Newton.

A central portion of the pad is provided with a retainer 26 of a rigid material. The retainer 26 comprises a semicircular recess 27 in which a distal end of an optical fiber 28 is arranged. The distal end of the optical fiber 28 is arranged in a compress 29 of a soft material, which is able to absorb a fluid such as blood.

The patch is attached to the skin of a patient with the compress 29 arranged at the skin surface adjacent or over the vascular access. The vascular access may extend in the opposite direction in relation to the optical fiber 28, so that the vascular access may be moved and even removed without influencing upon the patch and its attachment to the skin surface.

The exposed distal end of the optical fiber having it's covering peeled off is enclosed in the recess 27 of the retainer 26. The distal end of the optical fiber extends out of the recess 27 for a short distance. The retainer 26 further comprises wings 37 and 38, which are secured to the central portion of the patch, for example by means of an adhesive. In this manner, the optical fiber is firmly connected to the patch 21.

Figure 3:
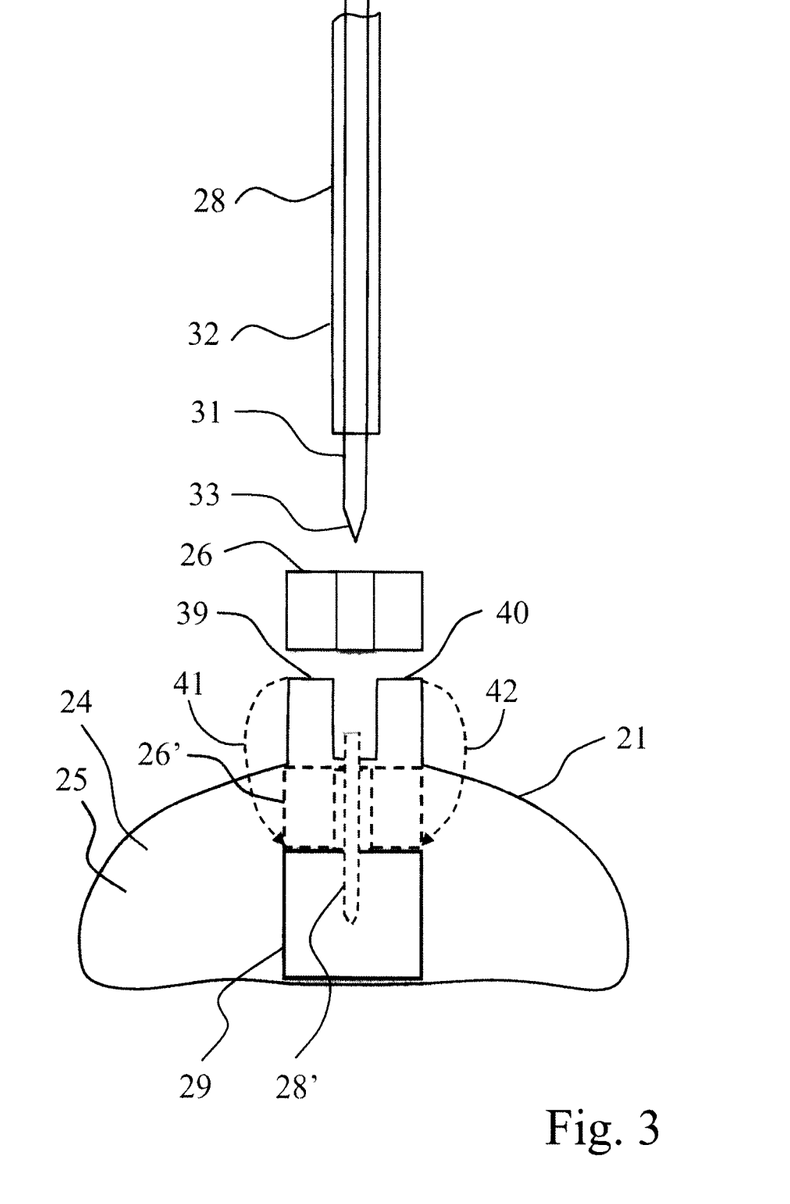
FIG. 3 is a plan view of the patient unit.

The patch 21 is shown in a plan view in FIG. 3. The patch comprises two lugs 39 and 40. When the retainer 26 is arranged in the position 26' shown in FIG. 3 by broken lines with the optical fiber in the recess 27, the lugs 39 and 40 are folded over the retainer wings 37 and 38 as shown by broken line arrows 41 and 42 in FIG. 3 and glued in place by an adhesive. The optical fiber may also be kept in place in the retainer recess by means of an adhesive. By means of the retainer 26, the distal end of the optical fiber will be firmly held in place in the middle of the patch as shown by broken lines 28' in FIG. 3.

Figures 4, 5, 6, 7, 8:
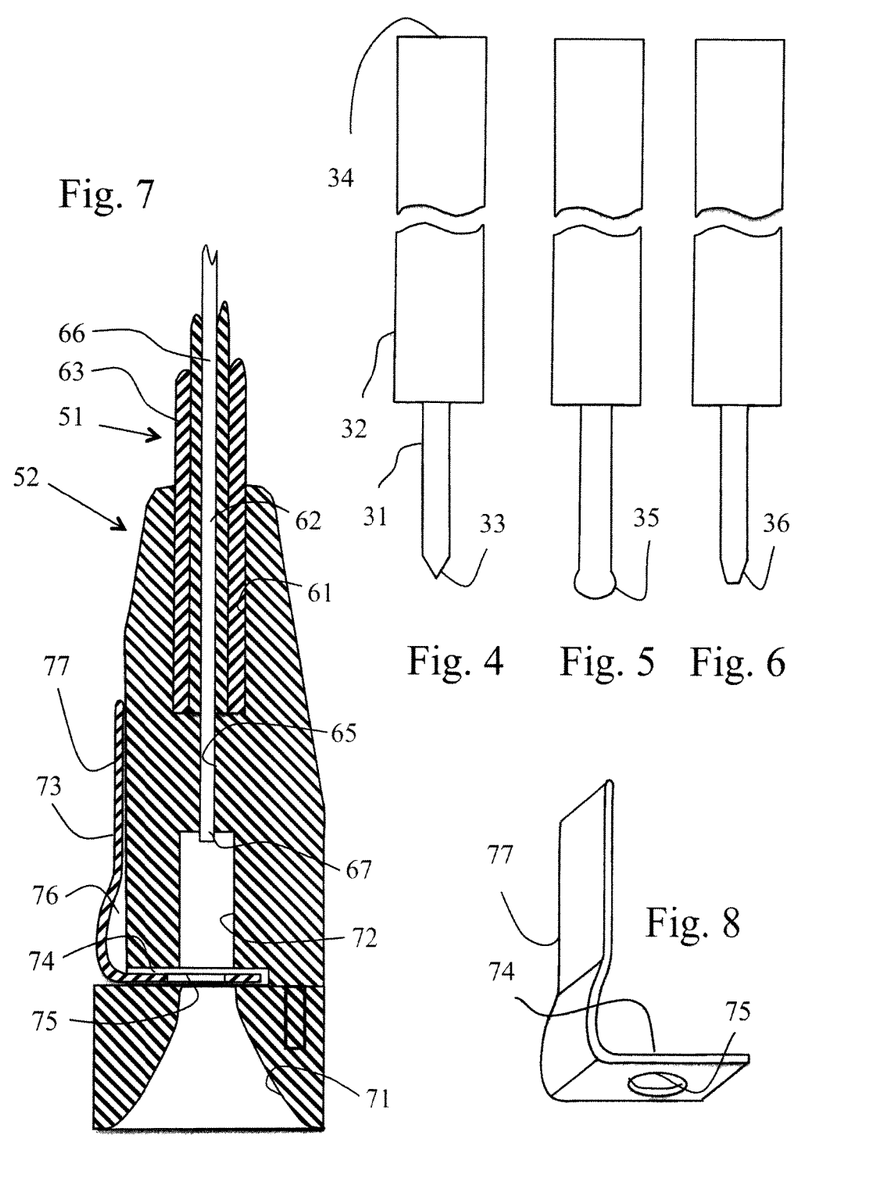
FIGS. 4, 5 and 6 are side views of a distal end of the patient optical fiber.
FIG. 7 is a cross-sectional view of the connector.
FIG. 8 is a perspective view of the spring member.

The optical fiber is shown in an enlarged side view in FIG. 4. The distal end 31 of the optical fiber is exposed by removing a covering 32 of the fiber over a portion adjacent the end thereof, such as over a length of about 12 mm. The semicircular recess 27 of the retainer 26 may have a length of 8 mm and the portion of the optical fiber extending out of the retainer 26 may be about 4 mm. The distal end of the patient optical fiber is shaped as a cone 33 by machining the end of the fiber, for example by laser or by mechanical operation. The cone angle is approximately 90 degrees. The total length of the patient optical fiber may be for example about 100 mm.

The proximal end 34 of the fiber is cut at a right angle. The patient fiber proximal end surface is machined so that it is sufficiently transparent for light as explained in more detail below. The outer diameter of the optical fiber may be approximately 2.2 mm and the optical core of the optical fiber may have a diameter of about 0.75 mm.

The optical fiber is selected to be of standard quality. The core is made of a plastics material having an index of refraction, which as about 1.5 (PMMA plastics). The optic core is transparent for light at a red wavelength, such as 690 nm. Such a fiber can be obtained from many manufacturers at a very low price, for example Toray Japan.

Optical fibers of other qualities may be used, such as a fiber with a glass core. However, the properties of the optical fiber may be selected so that a standard fiber may be used, which makes the price low.

The optical fiber is normally straight, without any bends. However, the optical fiber may be exposed to smaller bends without influencing upon the operation of the device.

In alternative embodiments, the distal end of the fiber may have another shape than conical, as long as almost complete total internal reflection is obtained at the distal end, when it is surrounded by air. Such a shape may be semi-circular or drip-shaped 35 as shown in FIG. 5 or frusto-conical 36 as shown in FIG. 6.

The compress 29 is attached over the exposed distal end of the patient optical fiber so that the distal end is embedded in the compress. When the compress comes into contact with a fluid, such as blood, the fluid will be sucked up by the compress and distributed inside the compress. When a predetermined amount of fluid, such as about 0.2 to 2 milliliters, have been absorbed by the compress, the fluid reaches the center of the compress and the distal end of the optical fiber enclosed therein. When the distal end of the optical fiber is exposed to or contacted by the fluid, the total internal reflection ceases.

The entire patient unit 12 is made in a manner so that it is as inexpensive as possible. The patient unit is disposable and is used only once per treatment. The patient unit should be sterilized.

The patient unit 12 is connected to the monitoring unit 16 by a connection unit 14.

The connection unit 14 does not need to be sterilized, since it is relatively far away from the wound or vascular access. The connection unit can be used several times and for different patients. However, certain facilities may want to use the same connection unit for the same patient, when the patient returns for successive treatments. A hemodialysis patient normally obtains dialysis treatment each second day, or trice per week. The connection unit may be used for several hundreds of treatments or more.

Consequently, the connection unit can be made to be more expensive than the patient unit, which is disposable.

The connection unit 14 essentially comprises an optical fiber 51 provided with a patient connector 52 at the distal end and a monitor connector 53 at the proximal end, see FIG. 1. The length of the connection optical fiber 51 may be for example 2 m, which is sufficient for attachment to a monitor unit 16 arranged at a dialysis machine. However, if the monitor unit is attached to the patient, for example at the arm of the patient, the connection unit may be much shorter, for example about 200 mm.

Figure 16:
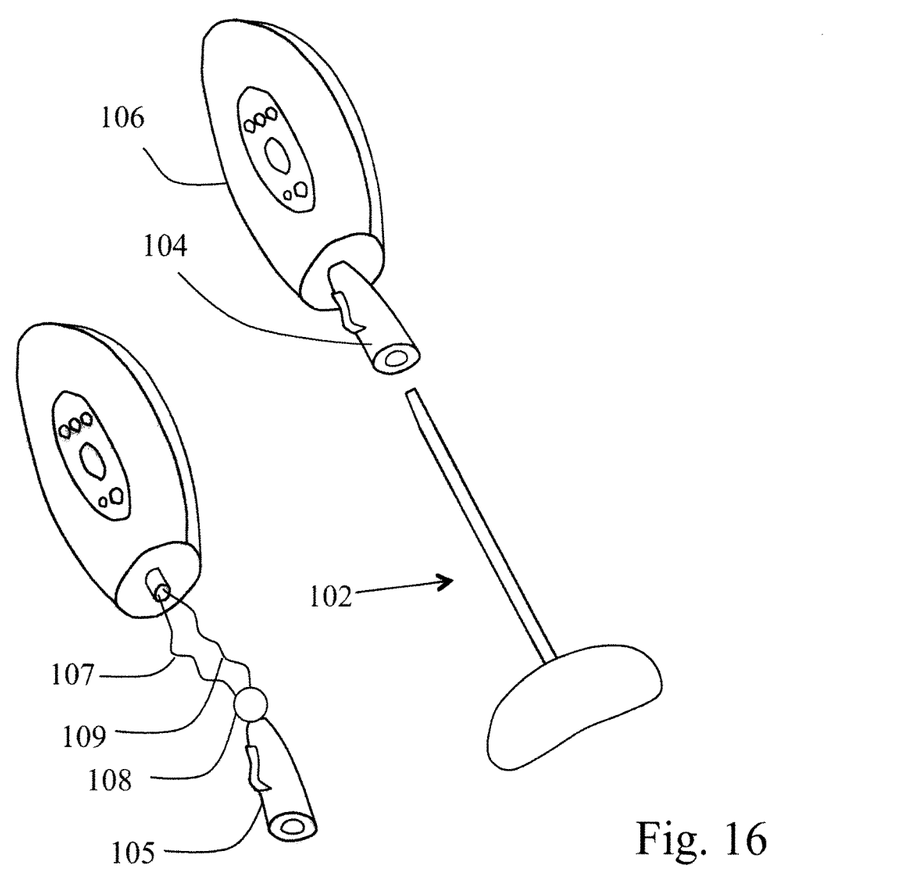
FIG. 16 is a perspective view similar to FIG. 1 of another embodiment.

In another embodiment, the connection unit is integrated in the monitor unit 16 so that the connector 52 is arranged in the monitor unit and extends out from the monitor unit. In this embodiment, the patient optical fiber may be longer, for example about 250 mm as shown in FIG. 16.

The connection optical fiber may be winded into a bundle 54 as shown in FIG. 1. It is important that the optical fiber is not bent too sharply.

Since the connection unit should be used several times, it should be able to withstand normally occurring cleaning agents at a hospital, such as alcohol and acids. The optical fiber may be arranged inside a tube made of a plastics material, which is normally used in hospital environments, such as PVC or an elastomer material. The tube material may be transparent so that damages of the optical fibers are visible if visible light is used.

The optical fiber should be protected from being exposed to a small radius, as may occur if the fiber is kinked or bent sharply. Thus, the connecting fiber may be arranged inside a holder, such as a bobbin having a spindle or cylinder with flanges as described in connection with FIG. 12 below.

The proximal end of the connection optical fiber comprises a standard connector 53 for connection to a light transmitter and receiver, as explained further below.

The distal end of the connection optical fiber comprises the patient connector 52 adapted for connection to the proximal end of the patient optical fiber 28.

The patient connector 52 is shown in more detail in FIG. 7. The upper end of the connector 52 as shown in FIG. 7 receives the connection optical fiber 51 as described above, in a cylindrical opening 61, which may have a diameter of about 3.25 mm in order to receive the connection optical fiber 62 having a diameter of 0.8 mm and a transparent hose 63 having an external diameter of 3.2 mm and a material thickness of about 1.1 mm. The distal end of the connection optical fiber extends through a small hole 65 having a diameter of 0.8 mm, which is equally large as the core of the connection optical fiber 66. The distal end 67 of the connection optical fiber 51 protrudes a few tenth of a millimeter out of the hole 65 as shown in FIG. 7. The optical fiber and the transparent hose are all secured inside the openings 61 and 65, for example by an adhesive.

The core 66 of the connection optical fiber is not provided with any covering but the transparent flexible hose 63. Thus, if the optical fiber is bent with a small radius, so that light leaks out of the fiber, such light will be visible through the hose 63. If the light is red, as in one embodiment, such a bend will be visible since the fiber glows with a red light at such a position.

The patient connector 52 is generally cylindrical and comprises at the bottom end seen according to FIG. 7, a conical entrance opening 71 for insertion of the proximal end of the patient optical fiber. The entrance is generally conical, so that the patient optical fiber end can easily be inserted into the entrance opening.

A cylindrical recess 72 is connected to the entrance, so that the patient optical fiber may be inserted into the cylindrical opening via the entrance opening 71. The cylindrical recess 72 has a diameter, which is slightly larger than the external diameter of the patient optical fiber, such as 2.3 mm.

Thus, the patient optical fiber can be inserted through the entrance and into the cylindrical opening. Then, the proximal end of the patient optical fiber will be arranged in line with and in contact with the distal end of the connection optical fiber, which is protruding from the narrow hole 65. In this way, light may be transmitted between the optical fibers.

It is important that the patient optical fiber is arranged in line with the connection optical fiber otherwise the transmission of light may be impaired. Thus, the cylindrical recess 72 has a length, which is adapted for ensuring that any mis-alignment between the optical fibers is as small as possible. A suitable length is about 10 mm.

Adjacent the transition between the entrance opening 71 and the cylindrical recess 72, there is arranged a spring member 73, which is further shown in perspective in FIG. 8. The spring member comprises a radial portion 74, which extends over the cylindrical recess 72 and at least partly occludes this recess 72. The radial portion 74 comprises a hole 75 having a diameter, which is slightly larger than the outer diameter of the patient optical fiber. The spring member 73 further comprises an operation portion 77 extending along the outer side of the connector as shown in FIG. 7. At the connection between the radial portion 74 and the operation portion 77, there is a bend over slightly more than 90 degrees so that there is formed a distance 76 between the spring and the connector. Upon pressure at said bend, the radial portion 74 is moved in the radial direction against the spring action of the spring member. During such a movement, the hole 75 in the radial portion 74 comes into register with the cylindrical recess 72 in the connector, whereby a patient optical fiber may be inserted in the cylindrical recess 72 as described above. When the pressure on the bend of the spring is relieved, the sides of the hole 75 will exert a pressure at the side surface of the patient optical fiber, thereby retaining the optical fiber in the connector.

The spring 73 and the hole 75 are dimensioned so that there is required a specific force for removing the patient optical fiber. This force is dimensioned so that the withdrawal force is smaller than the force required to remove the patch from the skin of the patient by pulling the fiber patient optical fiber. The adhesive of the patch may be dimensioned so that a force of about 30 Newton is required for removing the patch. In this case, the force required for withdrawing the patient optical fiber from the connector is smaller than 30 N, for example about 20 N. On the other hand, the force required for withdrawing the fiber from the connector should be sufficiently large for preventing unintended withdrawal of the fiber. Such a safe force would be about 10 N or larger. In other applications, a minimum safe force for withdrawing the fiber would be for example 15 N.

By this measure, it is ensured that the connector releases the patient optical fiber before the patch is removed from the patient, in case a large force acts upon the connection optical fiber. If this happens, it is easier to re-attach the optical fiber to the connector than to replace the patch on the skin of the patient.

If the patient optical fiber is withdrawn from the connector, this action results in the fact that the reflected light from the patient distal fiber end ceases. Thus, an alarm is initiated and the optical fiber may be re-attached or relocated into the connector. However, if the patch is removed from its position, without withdrawal of the optical fiber from the connector 52, this fact is not easily detected. Thus, it is an important safety feature that the optical fiber is withdrawn from the connector before the patch is dislocated.

The force from the spring member 73 acts upon the patient optical fiber in the radial direction. By this action, the optical fiber is forced against the side surface of the cylindrical recess 72. By this action, the patient optical fiber is arranged more closely in line with the connection optical fiber.

Figure 9:
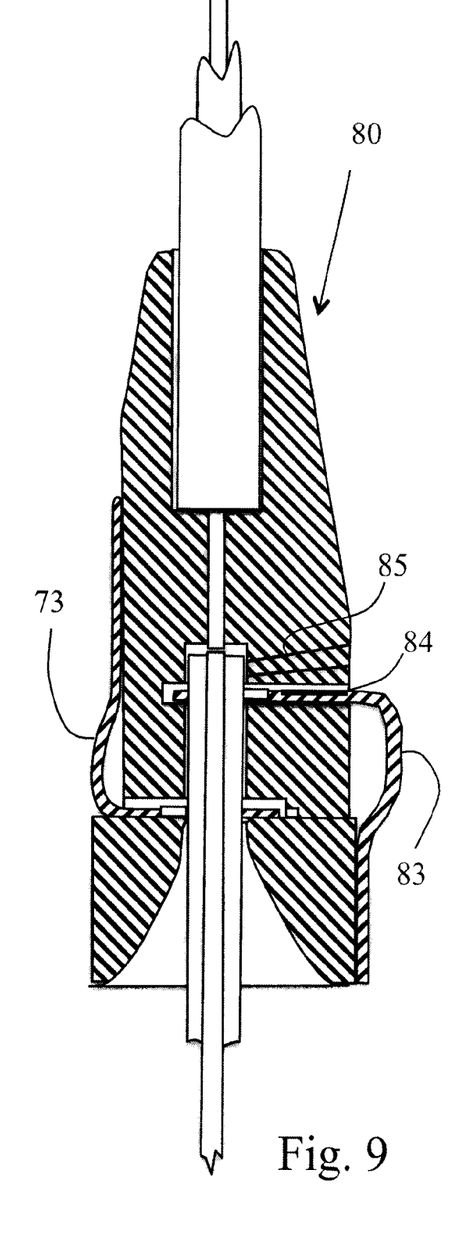
FIG. 9 is a cross-sectional view of another embodiment of the connector.

FIG. 9 is a cross-sectional view of an alternative patient connector unit 80. The connector unit 80 is substantially similar to the connection unit shown in FIG. 7. However, the connection unit 80 is provided with a second spring member 83 arranged opposite to the first spring member 73. Thus, the two spring members may be operated at the same time by a single hand of the user. By arranging two spring members, the safety is increased. In addition, it is ensured that the patient optical fiber is properly inserted into the cylindrical opening, because, if the patient optical fiber is not pushed entirely into the opening, the second spring member 83 will spring back to its original position. Such a spring back position may be indicated by a colored portion at the spring member at position 84. Thus, the portion of the spring 83 extending inside the connector unit 80 may have a red color. When the spring 83 is relieved, a part of the red color portion 84 becomes visible from the outside.

In addition, there may be arranged an inspection hole 85 extending from the point of contact between the patient optical fiber and the connection optical fiber. If there is improper contact, there will be a leakage of light, which is visible through the hole 85 as a red light, if red light is used in the optical fiber. Instead or in addition to the hole 85, there may be arranged light guides which guides the light out to the periphery of the connector, for example at several positions.

In addition, the monitor device is arranged to test the connection and indicate malfunction if the amount of light returned to the photo detector is smaller than expected. If the operation is normal, for example about 90% of the emitted light is sensed by the detector, whereby light is lost during the transmission through the optical fibers, in the connectors and at the distal end. When the distal end is contacted by or exposed to blood or a fluid, the detector signal decreases to about 25% to 40% of the emitted light during a relatively short time of about less than 1-2 seconds. If the detector is slowly exposed to fluid such as sweat, the signal level at the detector continuously decreases over a relatively long time, such as a decrease of about 10% or less over 10 seconds. If the patient optical fiber is withdrawn, the signal at the detector decreases to about 10% of the emitted light or even lower. Thus, the detector is able to differentiate between such conditions.

When the distal end of the patient optical fiber is exposed to blood, the light returned to the detector is mainly light, which has passed out into the blood and illuminates the blood. A part of the red light returned or scattered by the blood enters the patient optical fiber and is sent back to the detector.

If the patient optical fiber is withdrawn from the connector, there is substantially no light returned to the detector.

Figure 10:
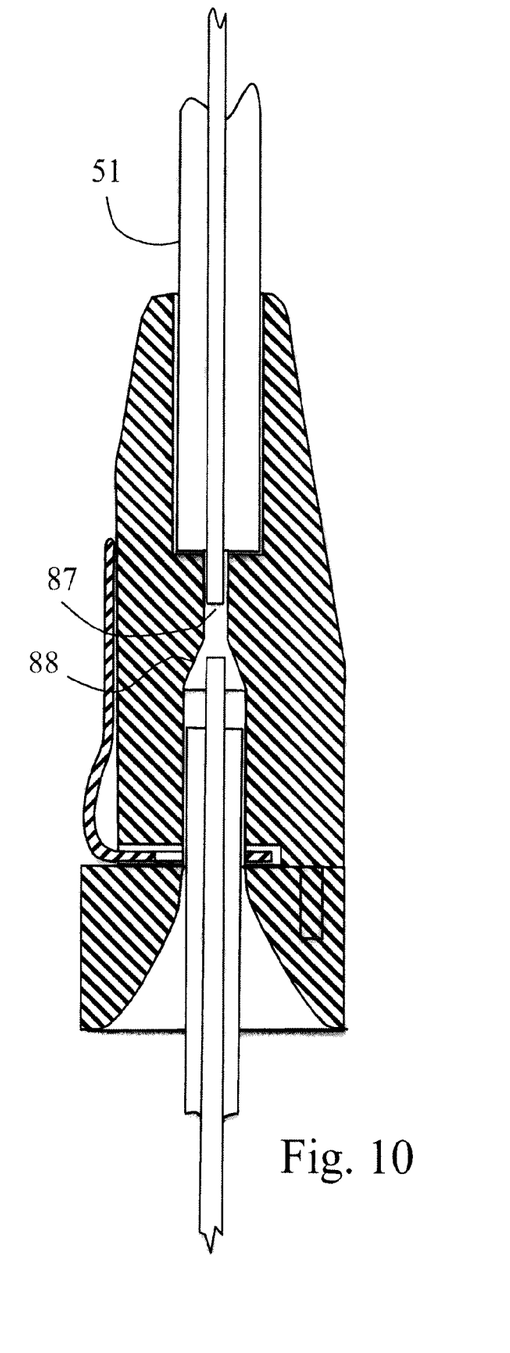
FIG. 10 is a cross-sectional view of a further embodiment of the connector.

FIG. 10 shows a further embodiment of the connector shown in FIG. 7. The connection optical fiber 51 is shorter and extends only partially through the hole 65 so that the distal end of the optical fiber ends at 87 as shown in FIG. 10. The end of the small hole 65 facing towards the patient optical fiber is chamfered as shown at 88, so that a conical entrance into the small hole 65 is obtained. The patient optical fiber is provided with a proximal end in which the covering 42 is partly peeled off and a portion of the core of the optical fiber is exposed. The core of the patient optical fiber extends into the hole 65 into abutment with the distal end of the connection optical fiber. Otherwise, the operation is substantially the same as the embodiment described with reference to FIG. 7.

Figure 11:
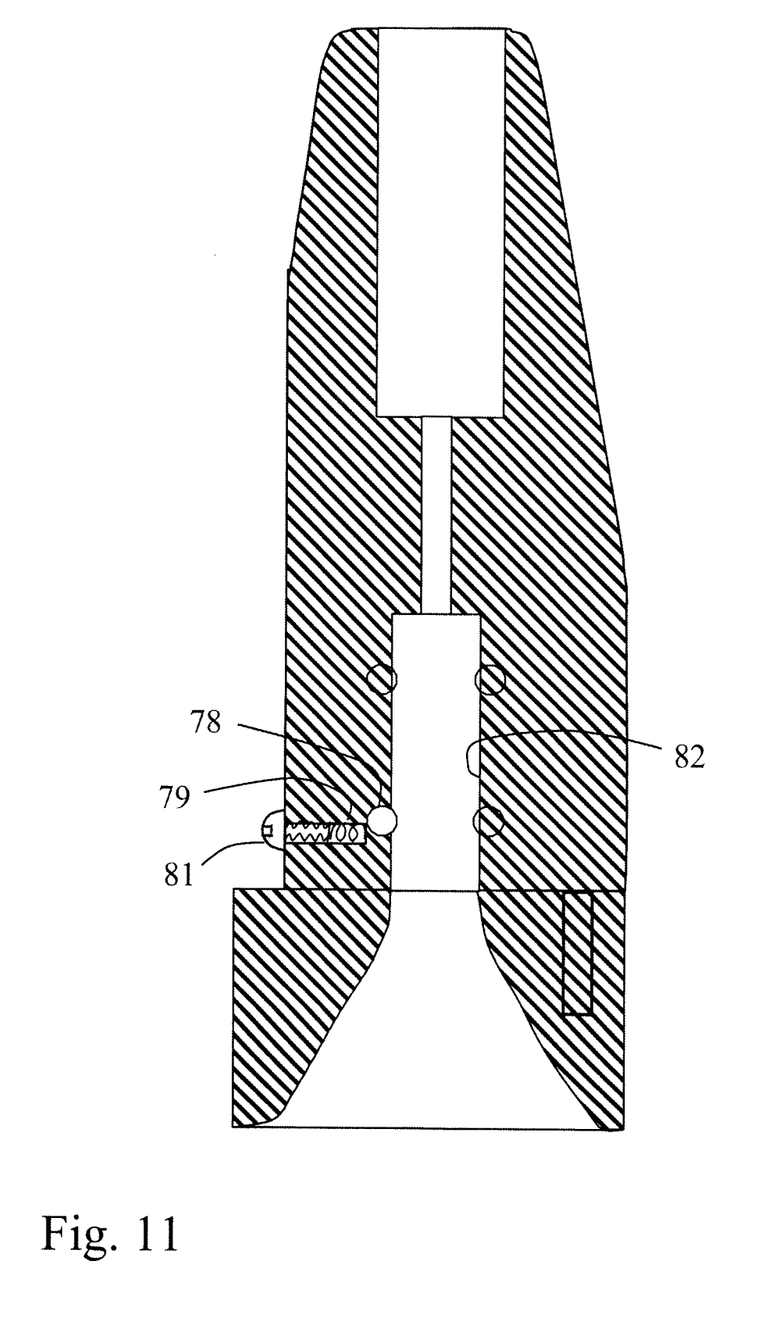
FIG. 11 is a cross-sectional view of a still further embodiment of the connector.

FIG. 11 is a cross-sectional view of another embodiment in which a withdrawal force is exerted by one or several rotational members 78. Each rotational member 78 is arranged so that rotation in one direction may take place without any restriction, but rotation in the opposite direction is prevented. Four rotational members 78 or rollers are shown in FIG. 11. The rotational members 78 are arranged so that insertion of a patient optical fiber into the cylindrical recess 82 may take place without any hindrance, since the rollers easily rotate in a corresponding direction. However, once entered, the optical fiber cannot easily be withdrawn, because the rollers are prevented from rotation in the direction in which the optical fiber is withdrawn. The rollers retain the optical fiber in the cylindrical recess 82 by friction. The frictional force exerted by the roller against the sidewall of the optical fiber is controlled by a spring 79, which acts upon the roller 82 as shown in FIG. 11 for one of the rollers. The force of the spring is adjusted by a screw 81. The other rollers may or may not be provided with similar spring and screw members. The rollers may be made of a slightly elastic material, such as rubber.

Figure 12:
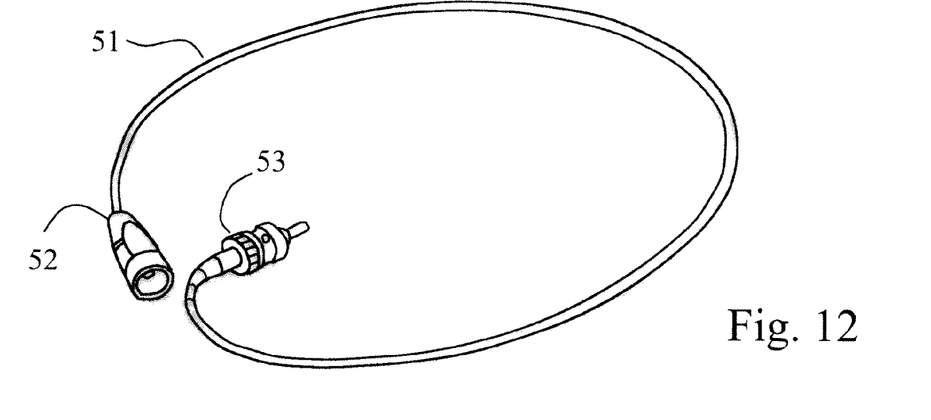
FIG. 12 is a perspective view of the connection optical fiber.

FIG. 12 is a perspective view of a connection optical fiber 51, provided with a patient connector 52 and a monitor connector 53. Only one revolution is shown in FIG. 12 but there may be several revolutions as shown in FIG. 1, depending on the length of the optical fiber 51.

Figure 13:
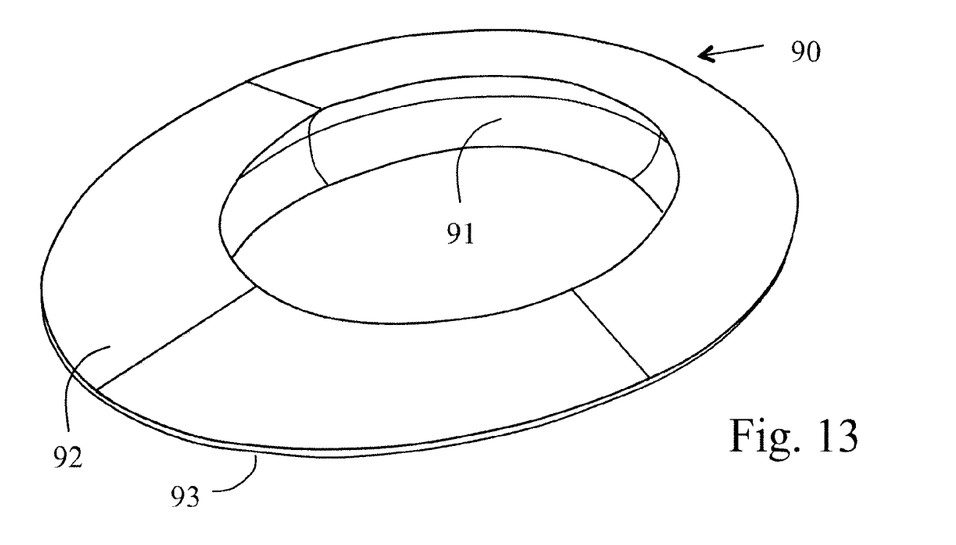
FIG. 13 is a perspective view of a bobbin.
Figure 14:
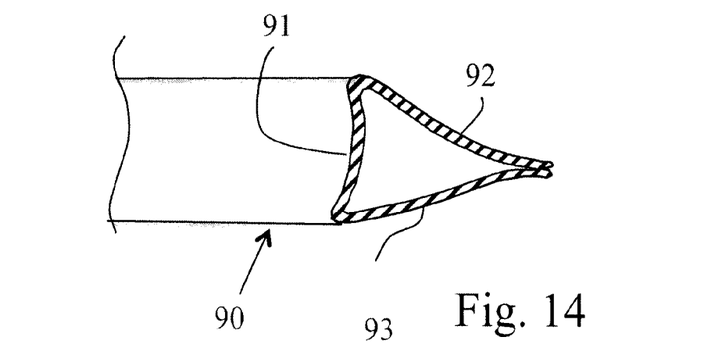
FIG. 14 is a cross-sectional view of a portion of the bobbin.

FIG. 13 is a perspective view of a bobbin 90 for enclosing the optical fiber 51 during transport and storage, between uses thereof. FIG. 14 is a cross-sectional view of the bobbin 90. As shown, the bobbin comprises a central portion 91, which is circular or oval. The inner wall of the central portion 91 may be slightly curved as shown in FIG. 14.

Two flanges 92 and 93 are attached at each end of the central portion 91. The flanges are inclined towards each other and form together with the central portion a triangular space, inside which the connection optical fiber may be arranged. The flanges are elastic so that they may be removed from each other and open the triangular space for insertion or removal of the optical fiber. The walls of the flanges 92 and 93 may be reinforced by springs made from wire and having the same shape as the cross-section and being arranged at suitable distances along the periphery of the bobbin.

Figure 15:
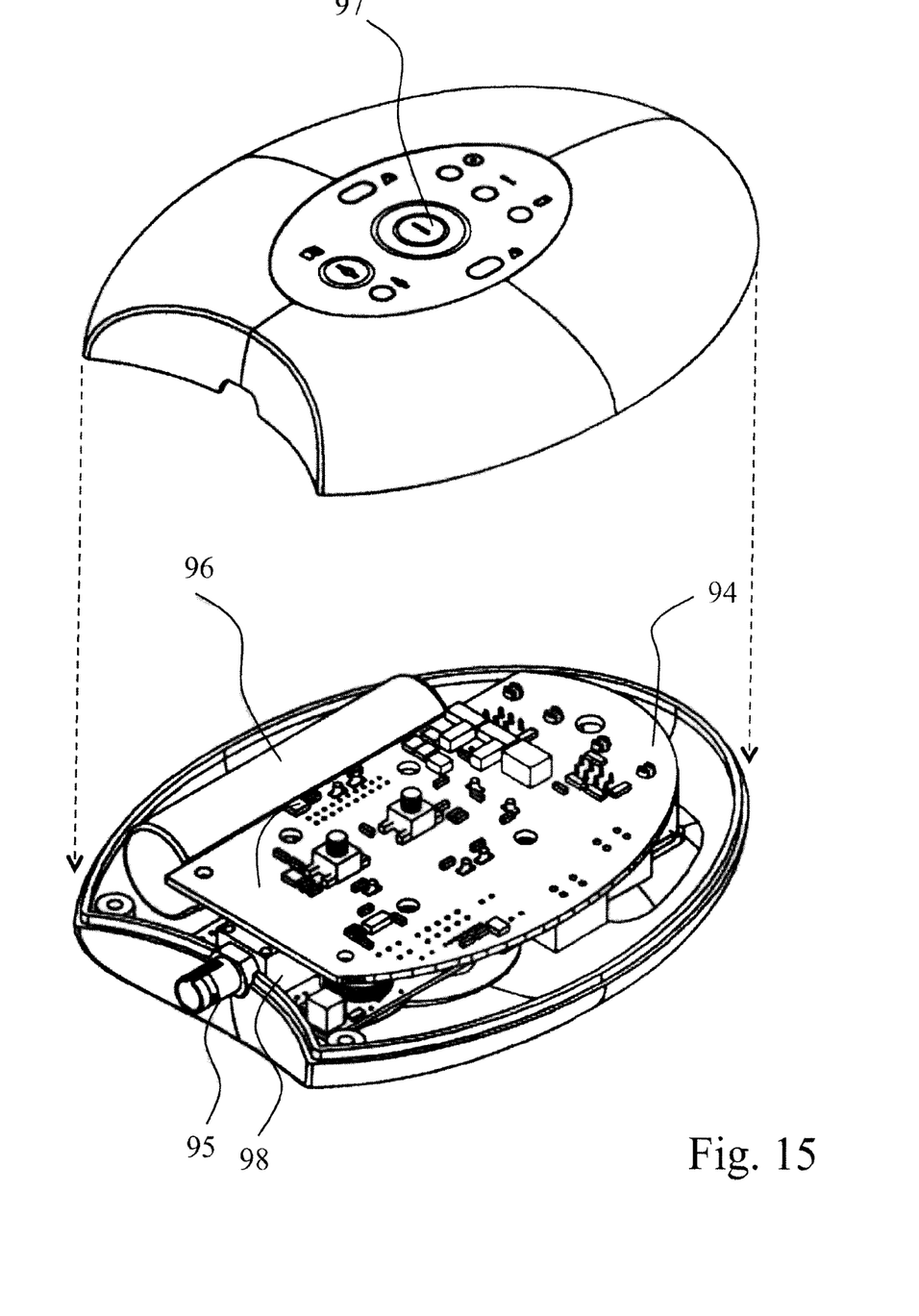
FIG. 15 is an exploded view of the monitor unit.

The central portion is arranged complementary to a monitoring device 16 shown in FIG. 15. The monitoring device is shown in an exploded view to shown the internal units of the monitoring device.

The outer shape of the monitoring device fits snuggly in the central portion 91. Because of the slightly curved inner surface of the central portion 91 as shown in FIG. 14, the central portion 91 is retained on the monitoring device.

The monitoring device comprises electronic circuits 94 arranged for performing the monitoring operation as described above. The exact arrangement of the electronic units is not critical, but has to fulfill all requirements of safe operation as required for medical device use in hospital or home care. The monitoring device comprises an optical module, comprising a female connector 95, a light source and a photo detector. The optical module 98 may for example by an optical unit of the type LD655 made by OECA, Germany, and comprises a 655 nm laserdiode and a Silicon PIN photodiode. Both units are coupled to a ST-Port for POF using a dielectrical beamsplitter.

The monitoring device further comprises a battery 96, a microprocessor (not shown) and several light emitting diodes LEDs and several switches. A piezo-electric buzzer (not shown) provides an audible alarm. In addition, a piezo-electric horn and driver (not shown) may be arranged for emitting a loud noise in a critical situation, sounding like a fire alarm signal.

At the middle of the monitoring device, there is arranged a start button 97 and at the bottom side of the monitoring module there are arranged several electrical connectors for connection to the hospital monitoring system or other external alarm system or other medical device. In addition, communication with the hospital monitoring system may take place by wireless devices.

The monitoring device is arranged to emit a light beam via the laserdiode into the connection optical fiber 51, which is connected to the female connector 95. The light is further transmitted from the connection optical fiber 51 to the patient optical fiber 31 via the patient connector 52. The light reaches the distal end of the patient optical fiber and is normally exposed to total internal reflection at the surfaces of the distal end. The light passes back along the patient optical fiber and to the connection optical fiber and finally reaches the photo detector.

If the distal end of the patient optical fiber is not covered with a fluid, almost all of the emitted light is reflected back to the photodiode. Only a small portion is lost because of transmission losses and in the two connectors. Normally, more than 90% of the emitted light is reflected back to the photo detector.

On the other hand, when the distal end is at least partly covered by blood, the light is not reflected by the conical surfaces and only a small portion, such as less than 50%, of the emitted light is returned to the photo detector. It is mainly light which is scattered and redirected by the blood back into the optical fiber which is returned. There is also a leakage in the connectors.

By monitoring the amount of light received by the photodiode, the presence of blood at the patch may be monitored. The device is very sensitive, since a large decrease in light received by the photodiode is obtained when the distal end is contacted by blood.

For example, the returned light is decreased to less than 50% when blood is sensed.

The compress may also absorb water, such as sweat. Water has substantially the same influence upon the optical properties of the distal end. Thus, if the compress is soaked with sweat or if water is spilled at the compress, a false alarm may be emitted. However, this problem may be solved by the electronic circuits and software in the monitoring device. Normally, the presence of sweat increases very slowly. Thus, a slow decrease in the returned light is an indication of the fact that sweat may disturb the monitoring operation. In such a situation, the monitoring device may emit an indication that the compress should be replaced.

If the signal decreases slowly, it is an indication of a situation that should not cause a blood alarm. Thus, a blood alarm signal is only generated if the decrease in returned light is sudden. For example, a decrease of returned light by more than 40% during less than 3 seconds may result in an alarm.

The bobbin is not required in certain applications, but the optical fiber may be sufficiently short as shown in FIG. 12 in order not to need to be winded, or may be winded outside the monitor unit.

In another embodiments, the connection unit and the monitor unit may form a single unit by having the connection optical fiber directly connected to the monitor unit without a monitor connector 53 or without a connection unit 14. Such an embodiment is shown in FIG. 16. The patient connector 104 is integrated in the monitor unit 106, and the patient optical fiber 102 is inserted directly into the patient connector 104 and withheld therein with a predetermined force, which is sufficiently low, such as 15N. The monitor unit 106 is attached to the arm of the patient, for example by a strap. The patient connector 104 may be connected to the monitor unit 106 with an elastic device so that the patient connector 104 is easily moveable over one or several centimeters in the longitudinal direction of the patient connector, in order to accommodate normal movements of the patient and the device.

Figure 17:
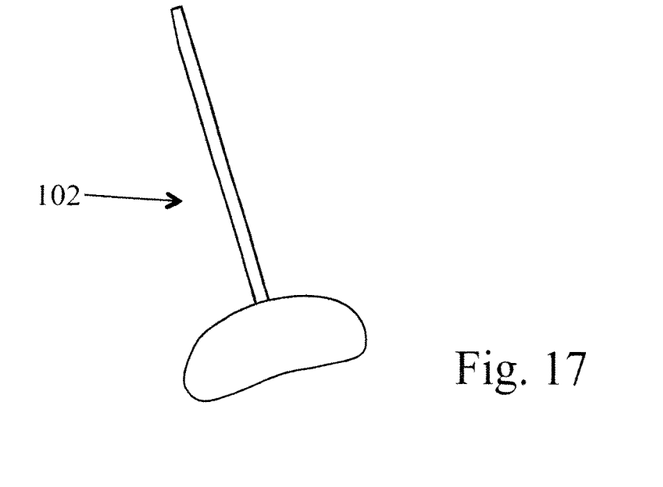
FIG. 17 is a perspective view similar to FIG. 1 of still another embodiment.

In still another embodiment shown in FIG. 17, the patient connector 52 may comprise the optical unit 98, see FIG. 15, which is now integrated in the patient connector. The optical unit 108 is shown only schematically as a circular unit. Several electrical wires 107 and 109 connect the optical unit 108 with the monitor unit 106 or 16. The patient connector 105 provided with the optical unit 108 is attached to the arm of the patient with a strap or tape.

The disposable patient unit can be made very inexpensively, since the patient optical fiber does not need any expensive machining or treatment. It is only required to form the distal end into a conical surface and to cut the proximal end at substantially 90 degrees. The surface of the exposed fiber core may need some machining so that any irregularities caused by the machining is removed, such as polishing. Often, the cutting and polishing can be made in one and the same step by a cutting disk. If the cutting action is performed by a laser, the surfaces normally do not need any post-treatment.

The length of the patient optical fiber is as small as possible, but so that the proximal end is sufficiently long away from the area to be kept sterile. Such a length may be about 100 mm.

Another type of patient unit 12 may be used, for example of the type shown in the patent documents WO 2006/001759 and WO 2008/123814. The patient optical fiber in these constructions is a double optical fiber extending in a loop. The proximal end of the double optical fiber may be inserted in a patient connector 52, which is modified so that the cylindrical recess 72 is oval. The connector optical fiber may comprise double fibers. Alternatively, the modified patient connector may comprise a beam splitter. In the embodiment of FIG. 17, the optical unit 108 may comprise a laser diode, which is arranged in line with one of the double optical fibers and a photo detector, which is arranged in line with the other optical fiber of the double optical fibers. Other modifications may arise to a skilled person.

The light used in the embodiment described above may comprise red light of a wavelength of about 630 to 690 nm. Many different commercial laser diodes are made by many different manufacturers and such laser diodes may be obtained at a low price. Also photo detectors are inexpensive for light in this wavelength area. Infrared light may be used as an alternative.

In the claims, the term "comprises/comprising" does not exclude the presence of other elements or steps. Furthermore, although individually listed, a plurality of means, elements or method steps may be implemented by e.g. a single unit. Additionally, although individual features may be included in different claims or embodiments, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

Although the present invention has been described above with reference to specific embodiment and experiments, it is not intended to be limited to the specific form set forth herein. Rather, the invention is limited only by the accompanying claims and, other embodiments than those specified above are equally possible within the scope of these appended claims.

The invention claimed is:

1. A device for monitoring a skin surface for leakage of blood at a monitoring position, comprising a patient unit, a connection unit and a monitor unit, wherein
the patient unit comprises a patch, including an adhesive layer, configured to be attached to the skin surface adjacent the monitoring position, wherein the adhesive layer is arranged to attach the patch to the skin surface wherein a predetermined removal force is required for removing the patch from the skin surface;
the patient unit further comprising a patient optical fiber having an exposed distal end arranged at the patch and a proximal end for connection to the connection unit;
the connection unit comprises a connection optical fiber, a distal end of which comprises a connector device having an opening passing through the connector device from one end to the other, wherein the connection optical fiber is arranged in one end of the opening and the patient optical fiber is insertable in the other end of the opening wherein a proximal end of the patient optical fiber is in contact with and in register with the distal end of the connection optical fiber,
wherein the connector device comprises a spring for exerting a force at the patient optical fiber at a side surface thereof for preventing withdrawal of the patient optical fiber, until a predetermined withdrawal force is exerted on the patient optical fiber, wherein the predetermined withdrawal force is smaller than said predetermined removal force.

2. The device according to claim 1, wherein said exerted force by the spring is sufficiently large for normally retaining the patient optical fiber in the connector, wherein a withdrawal force which is larger than 10N, is required for withdrawal of the patient optical fiber.

3. The device according to claim 1, wherein the exposed distal end of the patient optical fiber is arranged for reflecting back light passing along the patient optical fiber by total inner reflection when the exposed distal end of the patient optical fiber is surrounded by air.

4. The device according to claim 3, wherein the exposed distal end of the patient optical fiber has a shape which is at least one of: conical, frusto-conical and semi-spherical.

5. The device according to claim 1, wherein the opening passing through the connector device comprises a cylindrical opening for receiving the proximal end of the patient optical fiber, wherein said cylindrical opening has a diameter which is equal to or slightly larger than an outer diameter of the patient optical fiber.

6. The device according to claim 1, wherein the connection unit is integrated in the monitoring unit.

7. The device according to claim 1, wherein the connection unit comprises an integrated optical unit, which is connected with the monitoring unit via electrical wires.

8. The device according to claim 1, wherein said predetermined withdrawal force is smaller than 30 N.

9. The device according to claim 1, wherein said predetermined withdrawal force is smaller than 25 N.

10. The device according to claim 1, wherein said exerted force by the spring is sufficiently large for normally retaining the patient optical fiber in the connector, wherein a withdrawal force which is larger than 20 N is required for withdrawal of the patient optical fiber.

11. The device according to claim 1 wherein the monitoring position is located at a wound or a vascular access.

* * * * *